United States Patent
Li et al.

(10) Patent No.: US 9,101,685 B2
(45) Date of Patent: *Aug. 11, 2015

(54) CONTROLLED DRUG DELIVERY

(71) Applicant: Boston Scientific Scimed Inc., Maple Grove, MN (US)

(72) Inventors: Jianmin Li, Lexington, MA (US); Weenna Bucay-Couto, Burlington, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/190,675

(22) Filed: Feb. 26, 2014

(65) Prior Publication Data

US 2014/0242139 A1 Aug. 28, 2014

Related U.S. Application Data

(63) Continuation of application No. 10/209,476, filed on Jul. 31, 2002, now Pat. No. 8,685,427.

(51) Int. Cl.
```
A61F 2/00      (2006.01)
A61M 31/00     (2006.01)
A61F 2/06      (2013.01)
A61L 27/16     (2006.01)
A61F 2/07      (2013.01)
A61K 9/00      (2006.01)
```
(Continued)

(52) U.S. Cl.
CPC . *A61L 27/16* (2013.01); *A61F 2/07* (2013.01); *A61K 9/0024* (2013.01); *A61K 31/216* (2013.01); *A61K 31/407* (2013.01); *A61L 31/16* (2013.01); *A61L 31/18* (2013.01); *A61M 31/002* (2013.01); *A61F 2250/0067* (2013.01); *A61L 2300/602* (2013.01)

(58) Field of Classification Search
None
See application file for complete search history.

(56) References Cited

U.S. PATENT DOCUMENTS 4,186,745 A   2/1980  Lewis et al.
4,286,590 A   9/1981  Murase (Continued)

FOREIGN PATENT DOCUMENTS

EP   0734721 A2   10/1996
EP   0818207 A2    1/1998

(Continued)

OTHER PUBLICATIONS

Kertorolac. The Merck Index. 14th Ed. Accessed online on Nov. 3, 2008 at http://themerkindex.cambridesoft.com/TheMerck Index/index.asp.

Oxybutynin. The Merck Index. 14th Ed. Accessed online on Nov. 3, 2008 at http://themerkindex.cambridesoft.com/TheMerck Index/index.asp.

(Continued)

*Primary Examiner* — Ernst V Arnold
*Assistant Examiner* — Jianfeng Song
(74) *Attorney, Agent, or Firm* — Kacvinsky Daisak Bluni PLLC

(57) ABSTRACT

A medical device for placement in a body of a mammal is provided. The medical device comprises (1) a polymeric matrix forming the device and defining a lumen through the device, the matrix comprising polymer macromolecules and defining spaces between the polymer macromolecules; (2) a drug contained within at least some of the spaces of the matrix; and (3) a material contained within at least some of the spaces of the matrix to affect diffusion of the drug out of the polymeric matrix when the medical device is placed in the body of the mammal.

11 Claims, 6 Drawing Sheets

(51) Int. Cl.
*A61L 31/16* (2006.01)
*A61L 31/18* (2006.01)
*A61K 31/216* (2006.01)
*A61K 31/407* (2006.01)

(56) References Cited

U.S. PATENT DOCUMENTS

| | | |
|---|---|---|
| 4,589,880 A | 5/1986 | Dunn et al. |
| 4,957,479 A | 9/1990 | Roemer |
| 5,282,784 A | 2/1994 | Willard |
| 5,344,411 A | 9/1994 | Domb et al. |
| 5,509,900 A | 4/1996 | Kirkman |
| 5,527,337 A | 6/1996 | Stack et al. |
| 5,599,291 A * | 2/1997 | Balbierz et al. .................. 604/8 |
| 5,616,608 A | 4/1997 | Kinsella et al. |
| 5,647,843 A | 7/1997 | Mesrobian et al. |
| 5,696,034 A | 12/1997 | Katayama et al. |
| 5,762,638 A | 6/1998 | Shikani et al. |
| 6,039,967 A | 3/2000 | Ottoboni et al. |
| 6,143,314 A | 11/2000 | Chandrashekar et al. |
| 6,262,115 B1 | 7/2001 | Guittard et al. |
| 6,270,053 B1 | 8/2001 | Eshel |
| 6,335,028 B1 | 1/2002 | Vogel et al. |
| 6,364,852 B1 | 4/2002 | Lee |
| 6,545,097 B2 | 4/2003 | Pinchuk et al. |
| 6,796,960 B2 | 9/2004 | Cioanta et al. |
| 6,887,270 B2 | 5/2005 | Miller et al. |
| 2001/0007083 A1 | 7/2001 | Roorda |
| 2002/0045868 A1 | 4/2002 | Reever |
| 2002/0188246 A1 | 12/2002 | Hayner et al. |
| 2003/0040754 A1 | 2/2003 | Mitchell et al. |
| 2003/0060877 A1 | 3/2003 | Falotico et al. |

FOREIGN PATENT DOCUMENTS

| | | |
|---|---|---|
| EP | 1526879 B1 * | 7/2010 |
| GB | 2152382 A | 8/1985 |
| WO | 8601813 A1 | 3/1986 |
| WO | 95/06487 A2 | 3/1995 |
| WO | 95/08305 A1 | 3/1995 |
| WO | 00/62830 A2 | 10/2000 |

OTHER PUBLICATIONS

The Merck Index: An Encyclopedia of Chemicals, Drugs, and Biologicals, 1996, Merck Research Laboratories, 12th Edition, p. 932.

Konety, Badrinath et al., "Urolume Stent Placement for the treatment of postbrachytherapy bladder outlet obstruction," Urology 55: 721-724, 2000.

Vasudev, Sindhu C. et al., "Development of chitosan/polyethylene vinyl acetate co-matrix: controlled release of aspirin-heparin for preventing cardiovascular thrombosis," Biomaterials, 1997, vol. 18, No. 5, pp. 375-381.

Olweny, Ephrem O. et al., "Evaluation of a chronic indwelling prototype mesh ureteral stent in a porcine model," Urology 56 (5), 2000, pp. 857-862.

Gonzalez, Alex et al., "Minimiziing Hospital Length of Stay in Children Undergoing Ureteroneocystostomy," Urology 52 (3) 1998, pp. 501-504.

Medscape, Products and Devices in the Management of Urinary Incontinence: Indwelling Urinary Catheters and External Catheters, Society of Urological Nurses and Associates, 2003, pp. 1-3.

Liu, JS, Hrebinko, RL., "The use of 2 ipsilateral ureteral stents for relief of ureteral obstruction from extrinsic compression," Urol. Jan. 1998; 159(1) abstract, p. 1.

Fowler, Clare J., "Intravesical treatment of overactive bladder," Urology 55 (Suppl 5A): 60-64, 2000.

Arda, Serdar et al., "Urethral catheterization in Hypospadias Surgery: Should the device enter the bladder or be made a urethral stent," Journal of Pediatric Surgery, vol. 36, No. 12 Dec. 2001, pp. 1829-1831.

Young et al., "Covered, Retrievable, Expandable Urethral Nitinol Stent: Feasibility study in dogs," Radiology 2002 (Apr. 2002), 223: pp. 83-90.

Taniguchi, Takumi, et al., : Lidocaine attenuates the hypotensive and inflammatory responses to endotoxemia in rabbits, Critical Care Medicine, vol. 24(4) Apr. 1996), pp. 642-646.

Instill, Merriam-Webster, (Apr. 13, 2011), pp. 1-2.

Theodorou C et al., "Incontinence after surgery for benign prostatic hypertrophy: the case for complex approach and treatment," (Abstract) (1998).

* cited by examiner

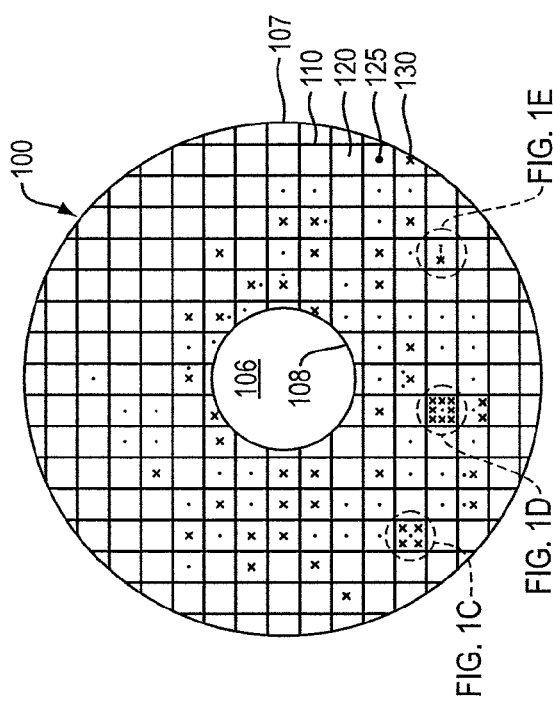
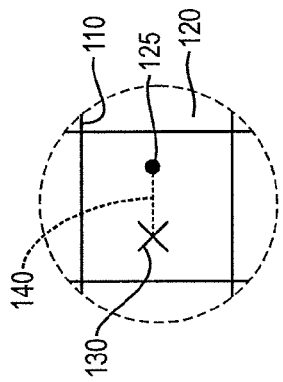
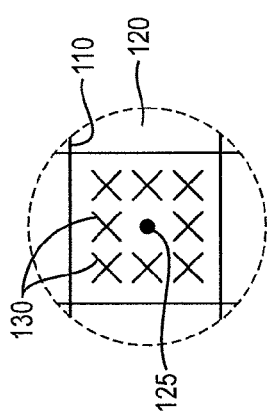
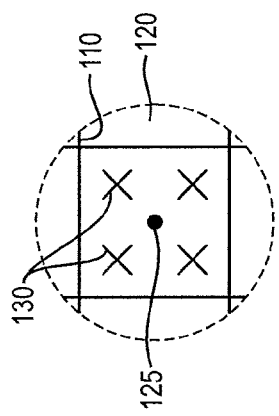
FIG. 1B
FIG. 1E
FIG. 1D
FIG. 1C

CONTROLLED DRUG DELIVERY

This application is a continuation of co-pending U.S. patent application Ser. No. 10/209,476, filed Jul. 31, 2002, entitled "Controlled Drug Delivery," which is hereby incorporated by reference in its entirety.

TECHNICAL FIELD

This invention generally relates to medical devices.

BACKGROUND INFORMATION

A drug can be delivered to a patient by a medical device. Drug-delivering devices generally release the drugs too fast or too slow to achieve desired therapeutic effects. The volume of drug released to the patient can exceed therapeutic, and even toxic, levels for example. Also, when a drug releases immediately from a medical device, additional doses of the drug may need to be delivered to the patient.

SUMMARY OF THE INVENTION

The invention relates to controlled delivery of one or more drugs to a body of a patient via a medical device placed in the patient's body. A medical device, according to the invention, can deliver one or more drugs over a desired period of time and at a desired level or volume. The invention allows the release of the drug(s) from the device in a controlled manner, both in terms of the release time and amount. For example, a relatively constant and therapeutic level of a drug can be released into the body from a device over a relatively long period of time, whereas other drug-delivering devices cannot achieve such a sustained and constant drug release profile.

In one aspect, the invention features a medical device for placement in a human or other mammal. The device comprises a polymeric matrix forming (entirely or partially) the device and defining a lumen through the device. The matrix comprises polymer macromolecules and defines spaces between the macromolecules. The device also comprises a drug contained within at least some of the spaces and a material contained within at least some of the spaces. The material affects diffusion of the drug out of the matrix when the device is placed in the body.

In one embodiment according to this aspect of the invention, the molecular weight of the material is greater than that of the drug, thereby hindering and prolonging diffusion of the drug out of the matrix. In another embodiment, the material chemically associates with at least the drug such that the drug must disassociate from the material before diffusing out of the matrix. The device can be a ureteral stent or a catheter, for example, and it can be placed entirely or partially within the patient's body.

In another aspect, the invention involves a hydrophobic polymeric matrix for coating (entirely or partially) a medical device. The polymeric matrix comprises polymer macromolecules and spaces between the macromolecules. A drug and a material are contained within at least some of the spaces, and the material affects diffusion.

In one embodiment according to this other aspect of the invention, the molecular weight of the material is greater than that of the drug, thereby hindering and prolonging diffusion of the drug out of the matrix. In another embodiment, the material chemically associates with at least the drug such that the drug must disassociate from the material before diffusing out of the matrix.

In yet another aspect, the invention relates to a method of drug delivery. The method comprises placing a device, entirely or partially, into a body of a human or other mammal. The medical device is capable of delivering a therapeutic level of a drug to the body at a predetermined time after the device is placed into the body. The method also comprises providing a second drug to the body prior to the predetermined time to deliver a therapeutic level of the second drug to the body before the predetermined time. In one embodiment, the medical device comprises a polymeric matrix as described above.

The foregoing and other objects, aspects, features, and advantages of the invention will become more apparent from the following description and from the claims.

BRIEF DESCRIPTION OF THE DRAWINGS

The drawings are not necessarily to scale, emphasis instead generally being placed upon illustrating the principles of the invention.

FIG. 1B is a cross-sectional view of one embodiment of a medical device according to the invention, taken along line 2-2 of FIG. 1A.

FIGS. 1C-1E are magnified views of the macromolecular structure of the polymeric matrix of an embodiment of a medical device according to the invention.

DESCRIPTION

In accordance with the invention, a medical device can be used as a vehicle to deliver one or more drugs to the body of a patient. A ureteral stent, catheter, and/or other medical device can be used to deliver the drug(s) by placing the device entirely or partially in the body of a patient. By using certain material(s) and drug(s) in a polymeric matrix, the diffusion of the drug(s) out of the matrix can be controlled in ways previously unachievable. The invention allows, for example, one or more drugs to be administered to the patient's body over a sustained time (ranging from days to months, for example) and at a relatively constant, and therapeutic, level.

A drug-delivering medical device according to the invention can be formed (entirely or partially) of a polymeric matrix, loaded with the drug(s) and material(s) that affect the diffusion of the drug(s) out of the matrix when the device is placed in the body of a human or other mammal. The device can be a ureteral stent, a catheter, a dialysis tube, a cannula, a urethral stent, a suture, or other medical device designed for placement (entirely or partially) in the body. A device according to the invention can alternatively be coated (entirely or partially) with such a loaded polymeric matrix. For example, a hydrophobic polymeric matrix can coat all or some portion of a lead wire, a stent, or a catheter.

Figure 1A:
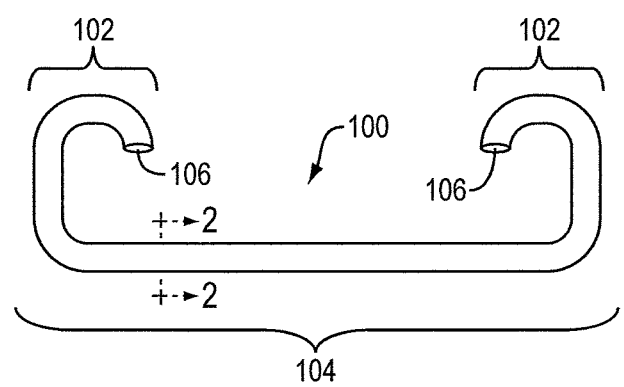
FIG. 1A shows an exemplary embodiment of a medical device according to the invention, specifically a ureteral stent.

FIG. 1A shows a ureteral stent 100 that includes two retention end portions 102, a central portion 104, and a lumen 106 extending through the length of the stent. A ureteral stent can be used for maintaining the patency of a patient's ureter to, for example, help drain urine from a kidney to the bladder in patients with ureteral obstruction or injury, or to protect the integrity of the ureter in a variety of medical procedures.

Figure 2:
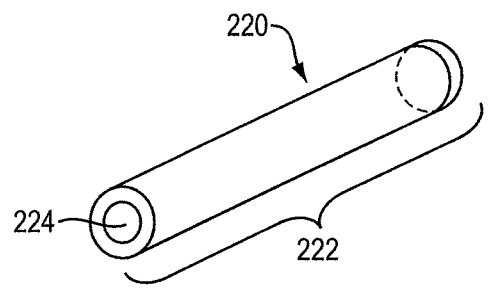
FIG. 2 shows another exemplary embodiment of a medical device according to the invention, specifically a tubular member such as a catheter or a portion of a catheter.

FIG. 2 shows a tubular member 220 that includes a tube 222 and a lumen 224 extending therethrough. The member 220 can be a portion of a catheter or it can be a urethral stent, for example, and it can be inserted percutaneously or through a natural body opening into a body cavity, duct, or vessel to allow the passage of a fluid and/or to distend a passageway. Catheters can be used to drain urine from the bladder, to deliver substances and/or remove blood from the vasculature, and to drain an abscessed area, for example. The stent 100, the member 220, and various other medical devices can be used to deliver drug(s) to a body, in accordance with the invention. Whatever the specific device used to deliver drug(s), the device can be formed (entirely or partially) of a loaded polymeric matrix and/or it can be coated (entirely or partially) by a loaded polymeric matrix, in accordance with the invention. The material(s) and drug(s) loaded within the matrix determine the diffusion rate and diffusion characteristics of the drug(s) when the device is placed, entirely or partially, within a body of a patient.

The polymeric matrix should be biocompatible with the patient's body. The polymer should possess the ability to withstand conditions of the inner body environment for the desired period of drug delivery. The polymer can, in fact, be biodegradable, but the degradation should not interfere with the desired course of drug release. Moreover, the polymer should be chemically and physically compatible with both the drug(s) and the material(s) contained therewithin. In addition, the polymer, whether forming the medical device itself or being a coating on a medical device should allow diffusion of body fluid, drug, and certain material into and out of the matrix. The polymeric matrix can be either hydrophobic or hydrophilic, and typically is hydrophobic when the loaded matrix is a coating on a medical device.

The polymeric matrix comprises primarily polymer macromolecules with naturally occurring spaces and voids interspersed throughout these macromolecules. These spaces naturally form a series of channels some of which may traverse from the matrix interior to the matrix surface. The total space that these voids encompass typically will be less than 0.1 cubic centimeters per gram of polymer. Within these spaces, drug(s) and material(s) reside. In one embodiment, both the drug(s) and material(s) exist together within at least some of the same spaces. The material(s) affect(s) diffusion of the drug out of the matrix when the device is placed (entirely or partially) within a body. The permeability of the matrix to body fluid and certain particles, in combination with the internal spaces allow, in part, for the absorption of body fluid(s) into the matrix and the release of drug(s) out of the matrix. Upon absorption of body fluid(s), swelling may occur and new spaces may be created, thereby further affecting drug diffusion from the matrix.

FIG. 1B shows a cross-section of the ureteral stent 100 (one example of a medical device according to the invention) of FIG. 1A taken along line 2-2. The ureteral stent is formed of a polymeric matrix 110. The stent 100 has an outer surface 107, in contact with body fluids of the mammal in which the device is placed (entirely or partially), and an inner surface 108 defining a lumen 106 passing through the stent 100. The polymeric matrix 110 comprises polymer macromolecules and defines spaces 120 between the polymer macromolecules. Many of these spaces 120 contain at least a drug 125 and another material 130, and many will contain both the drug 125 and the material 130. The material 130 affects diffusion of the drug 125 out of the matrix 110 when the stent 100 is placed in the body of the patient (a human or other mammal).

Figure 3:
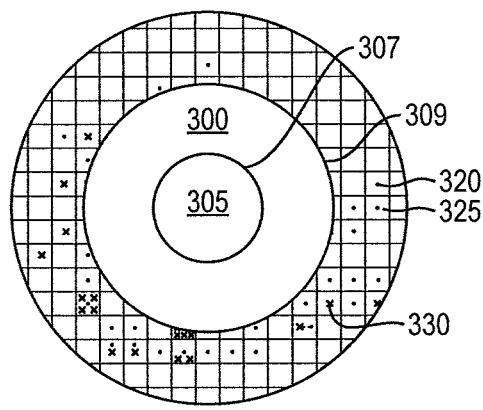
FIG. 3 is a cross-sectional view of one embodiment of a polymeric matrix coating the surface of a tubular medical device (e.g., a ureteral stent or a catheter) according to the invention.

FIG. 3 shows a cross-section of a tubular medical device 300 having an outer surface 309 in contact with a hydrophobic polymeric matrix 310 that coats the medical device 300 and an inner surface 307 that defines a lumen 305 passing through the device 300. The tubular medical device 300 may be a ureteral stent, a catheter, or a medical device designed for placement, entirely or partially, in the body. The polymeric matrix 310 comprises polymer macromolecules and defines spaces 320 between the polymer macromolecules. Many of these spaces 320 contain at least a drug 325 and another material 330, and many will contain both the drug 325 and the material 330. The material 330 affects diffusion of the drug 325 out of the matrix 310 when the medical device 300 and polymeric matrix 310 are placed within the body of the patient (a human or other mammal).

Figure 4:
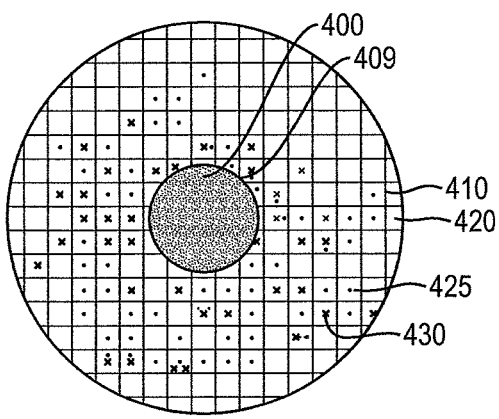
FIG. 4 is a cross-sectional view of one embodiment of a polymeric matrix coating the surface of a rod-shaped medical device (e.g., a lead wire) according to the invention.

FIG. 4 shows a cross-section of a rod-shaped medical device 400 having an outer surface 409 in contact with a hydrophobic polymeric matrix 410 coating the medical device 400 according to the invention. The medical device 400 may be a lead wire. The polymeric matrix 410 comprises polymer macromolecules and defines spaces 420 between the polymer macromolecules. Many of these spaces 420 contain at least a drug 425 and another material 430, and many will contain both the drug 425 and the material 430. The material 430 affects diffusion of the drug 425 out of the matrix 410 when the medical device 400 and polymeric matrix coating 410 are placed within the body of the patient (a human or other mammal).

Various polymers possess the characteristics described above and, thus, are suitable for forming the matrix according to the invention. These polymers include, but are not limited to, acyl substituted cellulose acetates and alkyl derivatives thereof, partially and completely hydrolyzed alkylene-vinyl acetate copolymers, unplasticized polyvinyl chloride, crosslinked homo- and copolymers of polyvinyl acetate, crosslinked polyesters of acrylic and methacrylate, polyvinyl alkyl ethers, polyvinyl fluoride, silicone, polycarbonate, polyurethane, polyamide, polysulphones, styrene acrylonitrile copolymers, crosslinked poly(ethylene oxide), poly (alkylenes), poly(vinyl imidazole), poly(esters), poly(ethylene terephthalate), and chlorosulphonated polyolefines. In one embodiment the polymeric matrix comprises ethylene vinyl acetate (EVA), commercially available from DuPont (Elvax 40W).

One or more drug(s) can be contained within the matrix. In general, any drug or combination of drugs that possess the ability to induce a desired effect within the body in which the device is placed can be used. Drugs that can be used include, but are not limited to, antispasmodic, local anesthetic, and non-steroidal anti-inflammatory (NSAID). In one embodiment, the drug comprises either oxybutynin chloride or ketorolac. Multiple drugs may be incorporated within the matrix, although for simplicity some of this description refers to a single drug.

The drug may be highly soluble. Highly soluble drugs tend to diffuse from a drug delivery device significantly faster than desired, and these can be controlled with release techniques according to the invention. The invention is applicable to less soluble drugs as well. The incorporation of certain materials, including, but not limited to, those that are either of low molecular weight or biodegradable, may serve to enhance the diffusion rate of less soluble drugs.

While the size and composition of the drug particle(s) are believed to impact the ability to control the drug diffusion rate out of the matrix, molecular weight is frequently used as a measure of the size of minute particles, and thus it is used here to help specify the range of drug particle size according to the invention. The drug(s) contained within the matrix, according to the invention, typically has a molecular weight less than about 1000. Loading, i.e., the quantity, of drug within the matrix varies according to the nature of the drug, the desired therapeutic effect, the desired period of drug delivery into the body, the quantity of the matrix, and the release profile of the diffusion-affecting material, among other factors. Drug loading may be between about 0.1 to 50 weight percent of the device depending on the above-identified factors. In one embodiment, drug loading is between about 2 to 20 weight percent of the device.

In addition to the drug(s), one or more other materials can be contained within the polymeric matrix. In general, any material or combination of materials that affect diffusion of the drug out of the matrix in a desirable way can be used. The material, generally, is a polymer or a biomaterial that affects drug diffusion based on its physical and/or chemical properties.

The material(s) can be selected based on the material's release profile. The release profile is a profile of the material's ability to affect drug diffusion out of the matrix over time, potentially determined by empirical analysis. The particle size of the material(s) may be the defining property for diffusion control and, as such, appropriate material(s) can be selected based on the molecular weight. The greater the molecular weight of the material(s), the more significantly the material will restrict drug diffusion out of the matrix. For example, assuming the drug incorporated within the matrix has a molecular weight of about 1000, the incorporation into the matrix of material(s) possessing a molecular weight of about 20,000 will tend to decrease the drug diffusion rate to a greater extent than the incorporation of material(s) possessing a molecular weight of about 2000. In such instances, the material(s) may have a molecular weight between about 1000 and 100,000. Selecting a material with a lower molecular weight than that of the drug tends to increase the diffusion rate of the drug out of the matrix. For example, the material can have a molecular weight of less than about 1000 when the drug has a molecular weight of about 1000.

The material's ability to associate chemically with the drug and, optionally, the polymeric matrix itself, may also serve as the drug diffusion-affecting mechanism. Where the incorporated material possesses such ability, the drug must overcome the barrier of the chemical association between the drug and the material, prior to diffusion of the drug out of the matrix. Such associations may be van der waals or ionic bonds. These associations are based on the polarity of the material, and also on the hydrophobic or hydrophilic nature of the material, the drug, and the polymeric matrix.

The material may be either soluble or nonsoluble. The material may also be biodegradable or non-biodegradable to achieve desired drug release into the body. Biodegradable material will control drug release for only that period, prior to excessive biodegradation, during which it is present in sufficient amounts. Biodegradable material can serve to increase drug diffusion from the matrix.

Loading of the material in the matrix may be between about 0 to 20 weight percent of the device depending on the nature of the material, the quantity of the matrix, the release profile of the material, the release profile of the drug, the desired drug diffusion effect, and the desired period for drug delivery, among other factors. In one embodiment, loading of the material is between about 1 to 10 weight percent of the device.

Suitable materials include, but are not limited to, styrenethylene-butylene-styrene (SIBS), collagen, alginates, carboxymethyl cellulose (CMC), hydroxypropyl cellulose (HPC), dextrin, plasticizers, lipophilic material and other fatty acid salts, pore formers, sugar, glucose, starch, hyaluronic acid (HA), chelating agents, including ethylenediaminetetraacetic acid (EDTA), polyethylene glycol (PEG), polyethylene oxide (PEO), and copolymers thereof. Multiple materials of varying release profiles may be incorporated within the matrix with the drug(s) to achieve the desired drug release profile.

A variety of methods can be used to manufacture a medical device or a coating according to the invention. For example, extrusion or injection molding can be used.

During extrusion, a molten state polymer is forced under high pressure through an opening, thus forming a medical device in the shape of the opening's cross-section. Initially, the solid polymer is melted by rotation of a screw and barrel under extreme heat, friction, and pressure. After the resulting molten polymer is forced through a pre-shaped die of desired cross-section, the extrudate is cooled either through immersion within a water bath or by exposure to air. Incorporation of the material(s) and drug(s) may occur prior to the extrusion process through precompounding with the polymer, or may occur as the polymer is melted during the actual extrusion process (Bridge, R., "Polymer Extrusion," URL: http://www.engr.uconn.edu/cheg/polymer/c256hnp.htm).

Injection molding provides a similar mechanical method to develop the medical device. During this process, an injection unit melts the polymer and subsequently injects the melt into a hollow mold cavity of desired shape. A ram fed injection molding machine contains a hydraulically operated plunger, first, to spread a thin layer polymer into a heated region; second, to converge the polymer melt at a nozzle; and lastly, to inject the melt into the mold. Alternatively, a reciprocation screw injection molding machine utilizes a hydraulically operated rotating screw to melt, mix and pump polymer after which, the screw serves as a plunger to inject the melt into the mold. Material(s) and drug(s) may be incorporated into the medical device by either precompounding both with the polymer, or alternatively, by addition during the melting process (Harris, L., "Injection Molding," URL: http://ww.engr.uconn.edu/cheg/polymer/injmold.htm).

In addition, various chemical processes can be used to manufacture the polymeric matrix. In a process known as imbibing, material(s) and drug(s) are incorporated into a pre-existing polymeric matrix. The polymeric matrix is immersed in a solution of desired concentration of drug(s), desired concentration of material(s) and appropriate solvent. Toluene, dimethylformamide (DMF) and methyl ethyl ketone (MEK), among others, provide effective solvent for the imbibing process. Upon immersion, the matrix swells as drug(s), material(s) and solvent penetrate into the matrix's network of channels and voids. Subsequently, solvent may be removed through ventilation, thereby entrapping the drug(s) and material(s) within the matrix.

Figure 5:
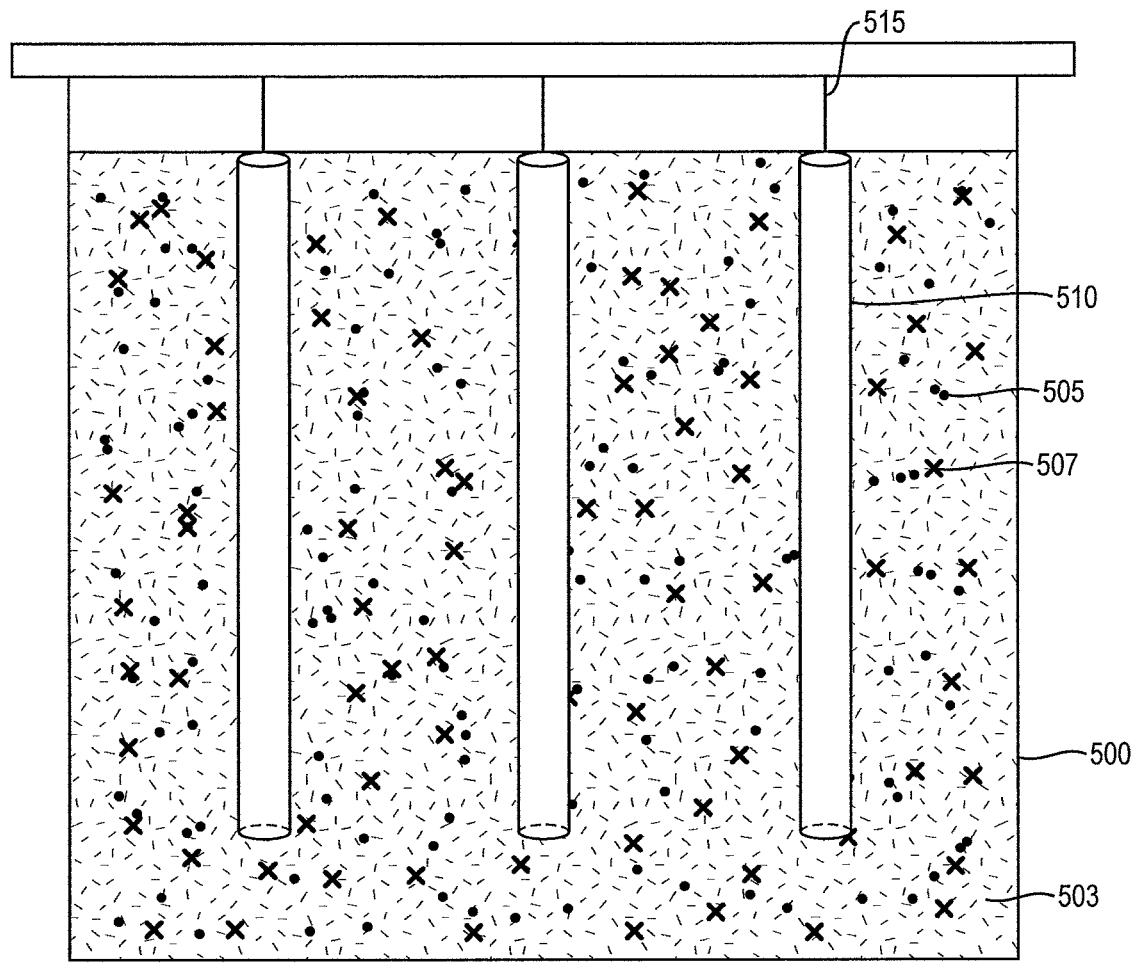
FIG. 5 depicts a container holding a solution of solvent, drug, and material, and it depicts a stage in the manufacture of a medical device in accordance with the invention.

Referring to FIG. 5, in imbibing, a container 500 holds a solution comprising solvent 503, drug 505, and material 507 and pre-formed polymeric medical devices 510 (e.g., several stents held in place by mandrels 515) are immersed within the solution to allow the drug 505 and the material 507 to imbibe into the swelling medical devices 510.

Solvent casting provides an alternative chemical method by which to manufacture the medical device. The desired amount of drug(s), material(s) and matrix polymer are dissolved in an appropriate solvent, e.g. methylene chloride, to form a casting solution. The resulting mixture is then charged into a mold of desired shape. Finally, the mold is dried, usually under vacuum, allowing the matrix polymer to recrystallize and form the device with material(s) and drug(s) contained within the interpenetrating spaces.

Applying a polymeric matrix coating to a medical device can involve dipping or spraying. For example, a mixture of solvent, polymer, drug(s), and material(s) can be applied to the medical device by a dipping or spraying mechanism. Subsequently, the solvent carrier is evaporated forming a polymeric matrix coating (containing drug(s) and material(s)) on the medical device surface.

Without being bound to any particular theory, it is believed that drug delivery out of the polymeric matrix operates by diffusion. Drug(s) reside within the spaces between the polymer macromolecules that comprise the polymeric matrix. When the matrix is placed in the body of a human or other mammal, body fluid permeates into the matrix. Swelling of the matrix with body fluid creates new spaces and channels. Body fluid carries drug out of the matrix and into the body. Absent proper control, the drug will diffuse out of the matrix at its natural rate, often too fast or too slow to achieve desired therapeutic effects. By incorporating the drug(s) and the other material(s) within the spaces of the polymeric matrix, in accordance with the invention, diffusion of the drug out of the matrix may be enhanced or restricted, as desired.

Figure 6:
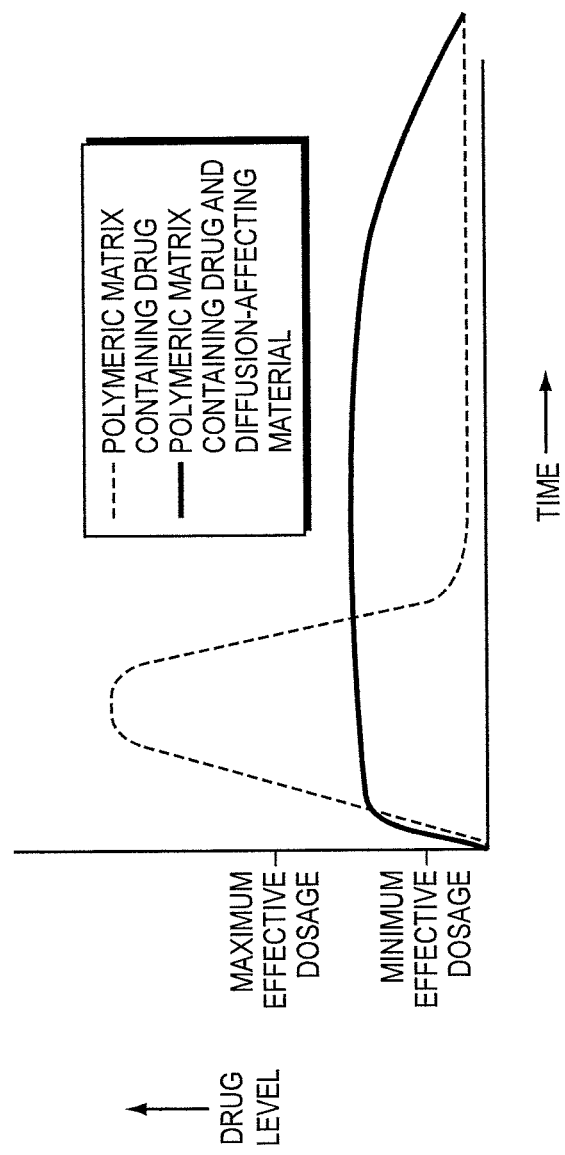
FIG. 6 is a graphical comparison of the drug release profile for a polymeric matrix containing drug and material according to the invention versus the drug release profile for a polymeric matrix containing only drug.

The material may restrict and prolong drug diffusion out of the matrix based on its physical and/or chemical properties. FIG. 6 is a graphical comparison of the drug release profile of a drug delivery medical device, according to the invention, containing both drug(s) and material(s) versus a drug delivery medical device containing merely drug(s) and no drug diffusion-affecting additional material(s). Without material(s) contained within the matrix, drug(s) may have a rapid burst drug release that can exceed therapeutic, or even toxic, levels. With the other material(s) contained within the matrix, drug diffusion can be restricted and prolonged at a therapeutic level.

The polymeric matrix may contain materials that restrict diffusion based on the material's size. Without being bound to any particular theory, it is believed that materials that have a molecular weight greater than that of the drug physically hinder diffusion of the drug out of the matrix. It is believed that such materials block the spaces and channels within the matrix, thereby restricting the drug's ability to diffuse out of the matrix. Materials with larger molecular weights serve as superior blocking agents, thereby restricting drug diffusion to an even greater extent.

The polymeric matrix may also contain materials that restrict diffusion of drug out of the matrix by chemically associating with the drug and, potentially, the matrix. The nature of the chemical association may be, but is not limited to, a van der waals or ionic bond. Certain materials may be selected based on their ability to form van der waals bonds with the drug and the matrix. Without wishing to be bound by any particular theory, it is believed that the van der waals interactions inhibit the mobility of the drug, thereby restricting diffusion of the drug out of the matrix. Body fluid may interfere with the bonds and promote diffusion of the drug out of the matrix. Ultimately, the recurring cycle of formation and breaking of bonds between the drug, the matrix and the material restricts diffusion of drug out of the matrix.

The molecular weight and the relative hydrophobic and/or hydrophilic properties of the material are important criteria for selection of material to associate with the drug and the matrix. Materials having the desired molecular weight and ratio of hydrophilic/hydrophobic groups are commercially available from Sigma-Aldrich Co. (St. Louis, Mo.) (www.sigma-aldrich.com). Materials with a greater molecular weight will likely possess larger hydrophilic and/or hydrophobic groups. As the desired groups increase in size, it is believed that the material will possess a greater likelihood of chemically associating with the drug and the matrix. Furthermore, it is believed that as the groups become larger, the strength of the material's chemical association with the drug and the matrix also increase, thereby further restricting diffusion of drug out of the matrix.

In addition, the hydrophobic and/or hydrophilic nature of the material can be a relevant criterion for material selection. Hydrophobic molecules form van der waals bonds with other hydrophobic molecules. Similarly, hydrophilic molecules form van der waals bonds with other hydrophilic molecules. Accordingly, the material(s) can be selected based on the relative hydrophilic and hydrophobic properties of the material(s), the drug(s) and, optionally, the matrix. For example, where both the drug and the matrix are hydrophobic, a material with more hydrophobic groups can be used so that the material forms van der waals bonds with both the drug and the matrix. The greater the material's ratio of hydrophobic groups to hydrophilic groups, the greater the likelihood that bonds will form, and the greater the affect on the drug diffusion rate will be. Alternatively, where the drug is hydrophilic and the matrix is hydrophobic, a material with both hydrophobic and hydrophilic groups may be selected such that the material may bond with both. In accordance with these embodiments, the material may be, but is not limited to, polyethylene glycol (PEG), polyethylene oxide (PEO), or copolymers thereof.

Materials may also be chelating agents. Chelating agents also possess the ability to associate with both the matrix and the drug, thereby restricting diffusion of the drug out of the matrix. Generally, bonds between chelating agents and each of the drug and the matrix are stronger than van der waals bonds. As a result, the use of chelating agents may have a greater effect on the drug diffusion rate. The material may be the chelating agent ethylenediaminetetraacetic acid (EDTA).

The material(s) may also be selected based on its polarity. Without wishing to be bound by any particular theory, it is believed that by incorporating nonpolar material within the polymeric matrix, the entry of body fluid, polar because of its substantial water content, into the matrix is restricted. Furthermore, it is believed that the nonpolar material creates a hydrophobic macroenvironment that shelters the drug from the hydrophilic body fluid that is necessary for drug to diffuse out of the matrix.

FIGS. 1C-1E show magnified views of the macromolecular structure of a polymeric matrix 110 containing drug 125 and material 130, according to the invention. Both the material and the drug reside within the spaces 120 between the polymer macromolecules of the polymeric matrix 110. In FIG. 1C, large molecular weight material 130 physically hinders the diffusion of drug 125 out of the polymeric matrix 110. In FIG. 1D, nonpolar material 130 creates a hydrophobic microenvironment that shelters the drug 125 from hydrophilic body fluid, thereby restricting diffusion of the drug 125 out of the polymeric matrix 110. In FIG. 1E, a chemical association 140 between the drug 125 and the material 130 restricts diffusion of the drug 125 out of the polymeric matrix 110.

Material contained within the spaces of the polymeric matrix may increase the diffusion of drug out of the polymeric matrix. The use of biodegradable or low molecular weight material may increase the drug diffusion rate. As the matrix swells with body fluid, biodegradable material will biodegrade quickly thereby creating new spaces and channels and increasing the drug diffusion rate. Similarly, low molecular weight material may diffuse out of the matrix prior to the diffusion of drug out of the matrix, opening new spaces and channels, and thereby increasing the drug diffusion rate. Low molecular weight materials include, but are not limited to, low molecular weight PEO and PEG, sugar, glucose, dextrin, starch, collagen, alginate and hyaluronic acid (HA).

The polymeric matrix medical device or a medical device coated entirely or in part with the polymeric matrix coating is placed within the body, possibly within a lumen. By way of example, but not limited to, the devices may be placed (either entirely or partially) within a body cavity, duct, or vessel. In one embodiment, the device, e.g. a ureteral stent, is placed within the ureter of the patient. Upon placement, body fluid enters the matrix and interacts with the drug(s) and the material(s). Subsequently, the drug(s) will diffuse out of the matrix at a rate determined, in part, by the chemical and/or physical properties of the material.

Another aspect of the invention is directed toward drug administration during the brief period between the placement of a drug delivery device within the body (either entirely or partially) and drug diffusion out of the device. Upon placement, drug should diffuse and achieve therapeutic levels within the body at a predetermined time. By directly providing a second drug which will achieve therapeutic levels within the body prior to the aforementioned predetermined time, one can effectively provide a continuous therapeutic dosage of drug. As an example, the drug release period from a drug delivery ureteral stent may be between 3 to 30 days. Direct instillation of drug, which takes effect about 2 to 24 hours after administration, can serve an important complementary role during the first few days following placement of the medical device within the body. The medical device may be a medical device with incorporated drug(s) and material(s) described above. However, the method of direct drug administration may be used with any drug-delivering medical device.

Figure 7:
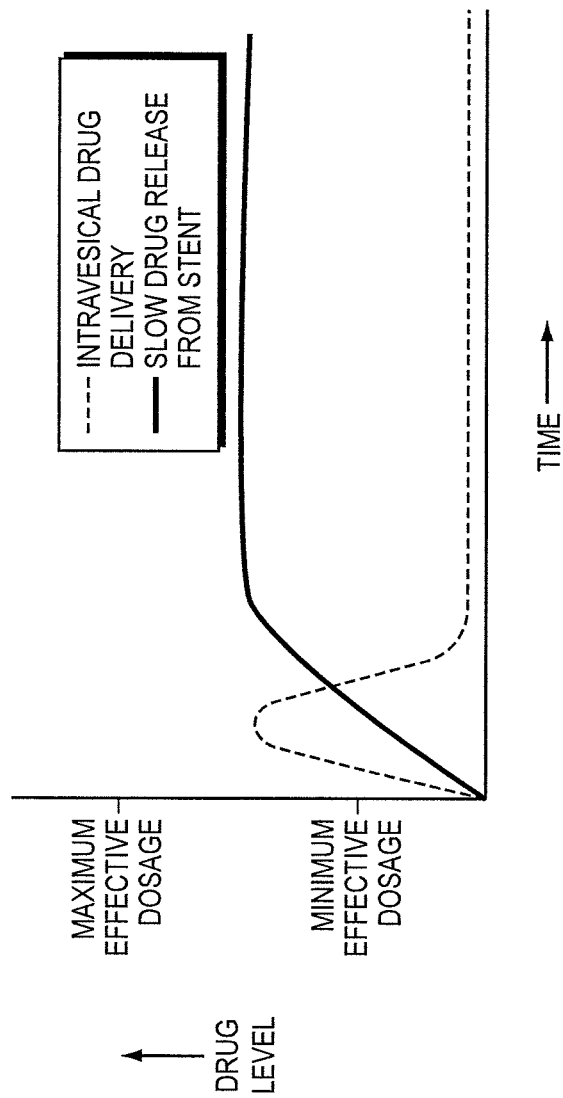
FIG. 7 is a graphical representation of the sustained therapeutic drug levels achievable by both placing a drug-delivering medical device and directly providing a drug.

FIG. 7 shows a graphical representation of this two step method of providing a continuous therapeutic level of drug to a patient. By providing intravesical drug delivery which achieves a therapeutic drug level prior to the predetermined time in which the drug released from the stent does so, a continuous and prolonged therapeutic level of drug may be administered to the patient.

The drug may be administered by direct intravesical drug instillation. The drug may also be administered via a ureteral catheter. By way of example, the drug may be administered locally, i.e., near the site of placement of the medical device. The drug may also be administered at the distal end of a placed ureteral stent or in the trigone area of the bladder, both of which are considered to be areas of great stent discomfort.

The drug administered directly may be either the same or a different drug from that incorporated within the placed medical device. Examples of drugs for use in this embodiment include, but are not limited to, antispasmodic, local anesthetic, nonsteroidal anti-inflammatory (NSAID), other anti-inflammatory drugs, calcium channel blockers, and other smooth muscle relaxants.

The invention is not to be limited only to the illustrative description provided herein. Variations, modifications, and other implementations of what is described herein will occur to those of ordinary skill without departing from the spirit and scope of the invention.

What is claimed is:

1. A medical device for placement in a body of a mammal, comprising:
    a polymeric matrix forming the device and defining a lumen through the device, the matrix comprising polymer macromolecules and defining spaces between the polymer macromolecules;
    a drug contained within at least some of the spaces of the matrix; and
    a material contained within at least some of the spaces of the matrix to affect diffusion of the drug out of the polymeric matrix when the medical device is placed in the body of the mammal, wherein each of the material (130) and the drug has a molecular weight, the molecular weight of the drug being less than the molecular weight of the material, and wherein the quantity of drug within the matrix is between 0.1 and 50 weight percent of the device.

2. The medical device of claim 1 wherein the medical device is a ureteral stent or a catheter.

3. The medical device of claim 1 wherein the polymeric matrix comprises ethylene vinyl acetate (EVA).

4. The medical device of claim 1 wherein the polymeric matrix is hydrophobic.

5. The medical device of claim 1 wherein at least some of the spaces that contain the drug also contain the material.

6. The medical device of claim 1 wherein the drug comprises oxybutynin chloride or ketorolac.

7. The medical device of claim 1 wherein the material comprises polyethylene glycol (PEG).

8. The medical device of claim 1 wherein the material is biodegradable.

9. The medical device of claim 1, wherein the material chemically associates with at least the drug such that the drug must dissociate from the material before diffusing out of the matrix.

10. The medical device of claim 1, characterized in that said polymeric matrix is coated onto the device.

11. The medical device of claim 10, wherein the medical device is a lead wire.

* * * * *